(12) United States Patent
Kropf et al.

(10) Patent No.: US 6,368,577 B1
(45) Date of Patent: Apr. 9, 2002

(54) NANOSCALE ORGANIC UV FILTERS

(75) Inventors: Christian Kropf, Duesseldorf; Hans Dolhaine, Glehn; Thomas Foerster, Erkrath; Bernd Fabry, Korschenbroich, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/456,369

(22) Filed: Dec. 8, 1999

Related U.S. Application Data

(60) Provisional application No. 60/111,834, filed on Dec. 11, 1998.

(51) Int. Cl.$^7$ .................................................. A61K 7/42
(52) U.S. Cl. ........................ 424/59; 424/401; 424/489; 424/490; 424/497
(58) Field of Search .......................... 424/401, 59, 489, 424/490, 497

(56) References Cited

U.S. PATENT DOCUMENTS

| | | | |
|---|---|---|---|
| 4,172,887 A | 10/1979 | Vanlerberghe et al. | 424/70 |
| 5,705,169 A | 1/1998 | Stein et al. | 424/401 |
| 5,730,960 A | 3/1998 | Stein et al. | 424/59 |
| 6,174,533 B1 * | 1/2001 | SaNogueira, Jr. et al. | 424/401 |

FOREIGN PATENT DOCUMENTS

| | | |
|---|---|---|
| DE | 1 165 574 | 3/1964 |
| DE | 20 24 051 | 5/1986 |
| EP | 693471 | 7/1995 |
| EP | 694521 | 7/1995 |
| EP | 818450 | 7/1997 |
| FR | 2 252 840 | 12/1978 |

OTHER PUBLICATIONS

P. Finkel, SÖFW–Journal, 122, 1996, pp. 543–548.
Mueller–Goymann, et al., Parf. Kosm., 79, 1998, pp. 24–26.
S. Cihlar, M. Tuerk and K. Schaber, Proceedings World Congress on Particle Technology 3, Brighton, 1998, pp. 1–11.
Todd, et al., "Volatile Silicone Fluids For Cosmetic Formulations", Cosm. Toil, 91, Jan., 1976, pp. 29–32.
Tronnier, et al., J. Soc. Cosmetic Chemists, 24, 1973, pp. 281–290.
Graham, et al., "Inhibition of the Mitochondrial Oxidation Of Octanoate By Salicyclic Acid And Related Compounds", J. Pharm. Pharmac., 26, 1974, pp. 531–534.
Lochhead, et al., "Encyclopedia of Polymers and Thickeners for Cosmetics", Cosmetics & Toiletries, 108, 1993, pp. 95–110.
"Kosmetische Faerbemittel", Farbstoffkommission der Deutschen Forschungsgemeinschaft, Verlag Chemie, Weinheim, 1984, pp. 81–106.

* cited by examiner

*Primary Examiner*—Jose' G. Dees
*Assistant Examiner*—Konata M. George
(74) *Attorney, Agent, or Firm*—John E. Drach; Steve J. Trzaska

(57) ABSTRACT

A cosmetic or pharmaceutical composition used for blocking the penetration of ultraviolet radiation, the composition containing nanoscale organic UV filters having a mean diameter of from 10 to 300 nm.

20 Claims, No Drawings

NANOSCALE ORGANIC UV FILTERS

CROSS-REFERENCE TO RELATED APPLICATIONS

This application claims priority from U.S. provisional application Serial No. 60/111,834, filed Dec. 11, 1998, the disclosure of which is incorporated herein by reference.

BACKGROUND OF THE INVENTION

This invention relates generally to nanoparticles and more particularly to the use of nanoscale UV filters in cosmetics.

UV filters (also known as protection factors) are organic substances which are capable of absorbing ultraviolet radiation and releasing the energy absorbed in the form of longer-wave radiation, for example heat. Substances of this kind are known in large numbers from the prior art and are used in particular in sunscreens and in other cosmetic products for hair care and body care to counteract the harmful effects of the sun such as, for example, erythemas, hyperkeratoses, skin ageing and, in the worst case, skin cancer. A corresponding overview of suitable UV filters was published by P. Finkel in SÖFW-Journal 122, 543 (1996); the use of nanoscale inorganic UV-blocking pigments is discussed by C. Müller-Goymann et al. in Parf. Kosm. 79, 24 (1998). So far as the consumer is concerned, there is an obvious need for effective sun protection, i.e. as long an exposure time as possible, which generally requires a particularly high percentage content of light filters in the formulation. To the manufacturer of such products, this represents a twofold problem because relatively large quantities of UV filters are difficult to incorporate in stable emulsions and, in addition, add significantly to their cost.

Accordingly, the problem addressed by the present invention was to improve the effectiveness of organic, preferably crystalline, topically applied UV filters by presenting them in new forms. At the same time, a way was to found of producing UV filter emulsions, particularly w/o emulsions, with a high content of UV filters in storage-stable form.

DESCRIPTION OF THE INVENTION

The present invention relates to the use of nanoscale organic UV filters with particle diameters of 10 to 300 nm for the production of cosmetic and/or pharmaceutical preparations.

It has surprisingly been found that the effectiveness of organic light filters can be significantly increased if they are present in the form of nanoparticles, i.e. particles with a mean diameter of 10 to 300 and preferably 50 to 150 nm. Accordingly, the quantity used can be reduced for the same sun protection effect. In addition, the effect of coating the particles with protective colloids is not only the absence of subsequent agglomeration, it also prevents any unwanted penetration of the nanofilters into the skin. In addition, the particle fineness of the filters even enables stable w/o emulsions with high light filter contents to be produced.

Organic UV filters

Nanoscale UV filters which may be used in accordance with the invention are, for example, organic substances which are liquid or solid, but preferably crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. According to the invention, it is preferred to use light filters which are solid and, in particular, crystalline at room temperature because they can readily be converted into nanoscale solid particles. However, filters liquid at room temperature may also be used. In this case, however, it is advisable to embed the nanoscale particles in a solid protective colloid matrix or to disperse them in a liquid carrier, for example a cosmetic oil, i.e. to prepare a nanodispersion.

Production of Nanoparticles

One such process for the production of nanoparticles by rapid expansion of supercritical solutions (RESS) is known from the article by S. Chihlar, M. Türk and K. Schaber in Proceedings World Congress on Particle Technology 3, Brighton, 1998. To prevent the nanoparticles from agglomerating, it is advisable to dissolve the starting materials in the presence of suitable protective colloids or emulsifiers and/or to expand the critical solutions into aqueous and/or alcoholic solutions of the protective colloids or emulsifiers or into cosmetic oils which may in turn contain redissolved emulsifiers and/or protective colloids. Suitable protective colloids are, for example, gelatine, casein, chitosan, gum arabic, lysalbinic acid, starch and polymers, such as polyvinyl alcohols, polyvinyl pyrrolidones, polyalkylene glycols and polyacrylates. Accordingly, the nanoscale organic UV filters preferably used are those which are surrounded by a protective colloid and/or an emulsifier. The protective colloids or emulsifiers are normally used in quantities of 0.1 to 20% by weight and preferably in quantities of 5 to 15% by weight, based on the UV filters.

Another suitable process for the production of nanoscale particles is the evaporation technique. Here, the starting materials are first dissolved in a suitable organic solvent (for example alkanes, vegetable oils, ethers, esters, ketones, acetals and the like). The resulting solutions are then introduced into water or another non-solvent, optionally in the presence of a surface-active compound dissolved therein, in such a way that the nanoparticles are precipitated by the homogenization of the two immiscible solvents, the organic solvent preferably evaporating. O/w emulsions or o/w microemulsions may be used instead of an aqueous solution. The emulsifiers and protective colloids mentioned at the beginning may be used as the surface-active compounds. Another method for the production of nanoparticles is the so-called GAS process (gas anti-solvent recrystallization). This process uses a highly compressed gas or supercritical fluid (for example carbon dioxide) as non-solvent for the crystallization of dissolved substances. The compressed gas phase is introduced into the primary solution of the starting materials and absorbed therein so that there is an increase in the liquid volume and a reduction in solubility and fine particles are precipitated. The PCA process (precipitation with a compressed fluid anti-solvent) is equally suitable. In this process, the primary solution of the starting materials is introduced into a supercritical fluid which results in the formation of very fine droplets in which diffusion processes take place so that very fine particles are precipitated. In the PGSS process (particles from gas saturated solutions), the starting materials are melted by the introduction of gas under pressure (for example carbon dioxide or propane). Temperature and pressure reach near- or super-critical conditions. The gas phase dissolves in the solid and lowers the melting temperature, the viscosity and the surface tension. On expansion through a nozzle, very fine particles are formed as a result of cooling effects.

Commercial Applications

Compared with conventional organic UV filters, the particular fineness of the particles provides for the more effective conversion of UV radiation into heat and hence for greater effectiveness after topical application. The nanoscale compounds are normally used in a quantity of 0.1 to 5% by weight, preferably in a quantity of 0.5 to 3% by weight and more preferably in a quantity of 1 to 2% by weight, based on the preparations.

Cosmetic and/or pharmaceutical preparations

The cosmetic preparations obtainable using the nanoscale organic UV filters in accordance with the invention, such as for example sun protection cremes, lotions, gels and the like, may contain mild surfactants, oils, emulsifiers, superfatting agents, pearlescing waxes, stabilizers, consistency regulators, thickeners, polymers, silicone compounds, biogenic agents, deodorizers, anti-dandruff agents, film-formers, preservatives, hydrotropes, solubilizers, inorganic UV-blocking pigments, antioxidants, insect repellents, self-tanning agents, perfume oils, dyes and the like as further auxiliaries and additives.

Typical examples of suitable mild, i.e. dermatologically compatible, surfactants are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic adds, alkyl oligoglucosides, fatty acid glucamides, alkyl amidobetaines and/or protein fatty acid condensates (preferably based on wheat proteins).

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-22}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons. These oils may even be used in the production of the nanoparticles where they serve as the medium into which the fluid solutions are expanded.

Suitable emulsifiers are, for example, nonionic surfactants from at least one of the following groups:

(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group such as, for example, Ceteareth-20, Ceteareth-12 or Ceteareth-20;

(2) $C_{12/18}$ fatty acid monoesters and diesters of adducts of 1 to 30 moles of ethylene oxide with glycerol;

(3) glycerol monoesters and diesters and sorbitan monoesters and diesters of saturated and unsaturated fatty acids containing 6 to 22 carbon atoms and ethylene oxide adducts thereof such as, for example, Glyceryl Stearate, Glyceryl Isostearate, Glyceryl Oleate, Sorbitan Oleate or Sorbitan Sesquioleate;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, Diisostearoyl Polyglyceryl-3 Diisostearate, Polyglyceryl-3 Diisostearate, Triglyceryl Diisostearate, Polyglyceryl-2 Sesquiisostearate or Polyglyceryl Dimerate. Mixtures of compounds from several of these classes are also suitable;

(7) adducts of 2 to 15 moles of ethylene oxide with castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) such as, for example, Polyglyceryl-2 Dihydroxystearate or Polyglyceryl-2 Diricinoleate;
(9) mono-, di- and trialkyl phosphates and mono-, di- and/or tri-PEG-alkyl phosphates and salts thereof;
(10) wool wax alcohols;
(11) polysiloxane/polyalkyl polyether copolymers and corresponding derivatives such as, for example, Cetyl Dimethicone Copolyol;
(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, such as, for example, Polyglyceryl-3 Glucose Distearate, Polyglyceryl-3 Glucose Dioleate, Methyl Glucose Dioleate or Dicocoyl Pentaerythryl Distearyl Citrate and
(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use are known from the prior art. They are produced in particular by reacting glucose or oligosaccharides With primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Coco-amidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$acyl sarcosine. Besides ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlescing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency regulators mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau GmbH), quaternized wheat polypeptides, polyethyleneimine, cationic silicone polymers such as, for example, Amidomethicone, copolymers of adipic acid and dimethylaminohy-droxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromo-butane, with bis-dialkylamines, for example bis-dimethylamino-1,3-propane, cationic guar gum such as, for example, Jaguar®, Jaguar®C-17, Jaguar®C-16 of Celanese, USA, quaternized ammonium salt polymers such as, for example, Mirapol®A-15, Mirapol®AD-1, Mirapol®AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, lithium, calcium, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing formulations and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula [$Al_2(OH)_5Cl$].$2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol, which is marketed under the name of lrgasan® by Ciba-Geigy of Basel, Switzerland, has also proved to be particularly effective.

Suitable antidandruff agents are climbazol, octopirox and zinc pyrethion. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clays minerals, Pemulen and alkyl-modified Carbopol types (Goodrich). Other suitable polymers and swelling agents can be found in R. Lochhead's review in Cosm. Toil. 108, 95 (1993).

Besides the soluble organic light filters mentioned, insoluble inorganic light-blocking pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg) also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type.

Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethyl methyl phenyl glycinate, allyl cydohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl and floramate.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be produced by standard hot or cold processes and are preferably produced by the phase inversion temperature method.

EXAMPLES

To prepare the nanoscale UV filters (Examples 1 to 5), carbon dioxide was taken from a reservoir under a constant pressure of 60 bar and purified in a column with an active carbon packing and a molecular sieve packing. After liquefaction, the $CO_2$ was compressed to the required supercritical pressure p by means of a diaphragm pump at a constant delivery rate of 3.5 l/h. The solvent was then brought to the necessary temperature T1 in a preheater and introduced into an extraction column (steel, 400 ml) which had been charged with the sterol or sterol ester. The resulting supercritical, i.e. fluid, mixture was sprayed through a laser-drawn nozzle (length 830 μm, diameter 45 μm) at a temperature T2 into a Plexiglas expansion chamber which contained a 4% by weight aqueous solution of an emulsifier or protective colloid. The fluid medium evaporated, leaving the nanoparticles dispersed in the protective colloid behind. To produce the nanoparticles of Example 6, a 1% by weight solution of Octocrylene in acetone was added dropwise to a 4% by weight aqueous solution of Coco Glucosides with vigorous stirring at 40° C. under a reduced pressure of 40 mbar. The evaporating solvent was condensed in a cold trap while the dispersion containing the nanoparticles remained behind. The process conditions and the mean particle size range (as determined photometrically by the 3-WEM methodor by laser scattering) are shown in Table 1 below.

TABLE 1

| Ex. | UV Filter | Solv. | p bar | T1 °C. | T2 °C. | Emulsifier/ Protective Colloid | PSR nm |
|---|---|---|---|---|---|---|---|
| | | | | | | Nanoparticles | |
| 1 | Sodium Phenylbenzimidazole Sulfonate | $CO_2$ | 200 | 80 | 175 | Polyvinyl alcohol | 40–100 |
| 2 | Benzophenone-3 | $CO_2$ | 180 | 70 | 160 | Polyethylene glycol (M = 400) | 60–120 |

TABLE 1-continued

| Ex. | UV Filter | Solv. | p bar | T1 °C. | T2 °C. | Emulsifier/ Protective Colloid | PSR nm |
|---|---|---|---|---|---|---|---|
| | | | | | | Nanoparticles | |
| 3 | Isoamyl-p-Methoxycinnamate | $CO_2$ | 200 | 85 | 180 | Polyvinyl alocohol | 70–130 |
| 4 | Octylmethoxycinnamate | $CO_2$ | 200 | 85 | 175 | Chitosan | 50–140 |
| 5 | Octyl Triazone | $CO_2$ | 200 | 85 | 175 | Coco Glucosides | 50–150 |
| 6 | Octocrylene | — | — | — | — | Coco Clucosides | 65–120 |

Table 2 below contains a number of Formulation Examples using UV filter nanoparticles.

TABLE 2

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Dehymuls ® PGPH Polyglyceryl-2-Dipolyhydroxystearate | 2.0 | 3.0 | — | 5.0 | — | — | — | — | — | — |
| Lameform ® TGI Polyglyceryl-3-Diisostearate | 4.0 | 1.0 | — | — | — | — | — | — | — | — |
| Ambil ® EM 90 Cetyl Dimethicone Copolyol | — | — | 3.0 | — | — | — | — | — | — | — |
| Emulgade ® PL 68/50 Ceteryl Glucoslde (and) Cetearyl Alcohol | — | — | — | — | 4.0 | — | — | — | 3.0 | — |
| Eumulgin ® B2 Ceteareth-20 | — | — | — | — | — | — | — | 2.0 | — | — |
| Tegocare ® PS Polyglyceryl-3 Methylglucose Distearate | — | — | — | — | — | — | 4.0 | — | — | — |
| Eumulgin VL ® 75 Polyglyceryl-2 Dipolyhydroxy stearate (and) Lauryl Gluooside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS Glyceryl Stearate | — | — | — | — | — | 2.0 | 4.0 | — | — | 4.0 |
| Lanette ® O Cetearyl Alcohol | — | — | 2.0 | — | 2.0 | 4.0 | 2.0 | 4.0 | 4.0 | 1.0 |
| Antaron ® V 216 PVP/Hexadecene Copolymer | — | — | — | — | — | 3.0 | — | — | — | 2.0 |
| Plantaren ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Dioctyl Carbonate | 5.0 | 4.0 | 6.0 | 8.0 | 6.0 | 5.0 | 4.0 | 3.0 | 4.0 | 6.0 |
| Cetiol ® J 600 Oleyl Erucate | 2.0 | — | 3.0 | 5.0 | 4.0 | 3.0 | 3.0 | — | 5.0 | 4.0 |
| Cetoil ® OE Dicaprylyl Ether | 3.0 | — | — | — | — | 1.0 | — | — | — | — |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Panthenol/Bisabolol | 1.2 | 1.2 | 1.2 | 1.2 | 1.2 | 1.2 | 1.2 | 1.2 | 1.2 | 1.2 |
| Generol ® 122 N Soja sterols | 0.5 | 1.0 | 1.0 | 2.0 | 1.0 | 1.0 | 1.0 | 2.0 | 0.5 | 2.0 |
| Sodium Phenylbenzimidazole Sulfonate acc. to Example 1 | 3.0 | — | — | 3.0 | — | — | 2.0 | — | 2.0 | — |
| Benzophenone-3 acc. to Example 2 | 1.5 | — | — | 2.0 | 1.5 | — | — | — | 2.0 | |
| Isoamyl p-Methoxycinnamate acc. to Example 3 | 5.0 | — | 4.0 | — | 2.0 | 2.0 | 4.0 | 10.0 | — | — |
| Octyl Methoxycinnamate acc. to Example 4 | 4.0 | — | 4.0 | 3.0 | 2.0 | 3.0 | 4.0 | — | 10.0 | 2.0 |

TABLE 2-continued

| Cosmetic preparations (water, preservative to 100% by weight) | | | | | | | | | | |
|---|---|---|---|---|---|---|---|---|---|---|
| Composition (INCI) | 1 | 2 | 3 | 4 | 5 | 6 | 7 | 8 | 9 | 10 |
| Octyl Triazone acc. to Example 5 | 2.0 | 4.0 | 3.0 | 1.0 | 1.0 | 1.0 | 4.0 | 3.0 | 3.0 | 3.0 |
| Octocrylene acc. to Example 6 | — | 5.0 | — | — | — | 4.0 | 5.0 | — | — | 10.0 |
| Zinc Oxide | — | 6.0 | 6.0 | — | 4.0 | — | — | — | — | 5.0 |
| Titanium Dioxide | — | 2.0 | 2.0 | — | — | — | — | 5.0 | — | — |
| Glycerine (86% by weight) | 5.0 | 5.0 | 5.0 | 5.0 | 5.0 | 5.0 | 5.0 | 5.0 | 5.0 | 5.0 |

(1) w/o Sun protection creme, (2–4) w/o sun protection lotion, (5, 8, 10) o/w sun protection lotion, (6, 7, 9) o/w sun protection creme

What is claimed is:

1. A composition comprising nanoscale organic UV filters having a mean diameter of from 10 to 300 nm.

2. The composition of claim 1 wherein the nanoscale organic UV filters are obtained by:
   (a) providing an organic UV filter starting material;
   (b) dissolving the organic UV starting material in a solvent under supercritical or near-critical condition to form a fluid mixture;
   (c) expanding the fluid mixture through a nozzle into a medium selected from the group consisting of a vacuum, a gas, a liquid, or combinations thereof; and
   (d) evaporating the solvent simultaneously with step (c) to form the nanoscale organic UV filters.

3. The composition of claim 1 wherein nanoscale organic UV filters are surrounded by a protective colloid.

4. The composition of claim 3 wherein the protective colloid is selected from the group consisting of polyvinyl alcohol, polyethylene glycol, and mixtures thereof.

5. The composition of claim 1 wherein the nanoscale organic UV filters are present in the composition in an amount of from 0.1 to 5% by weight, based on the weight of the composition.

6. The composition of claim 1 wherein the nanoscale organic UV filters have a mean diameter of from 50 to 150 nm.

7. The composition of claim 3 wherein the protective colloid is present in an amount of from 0.1 to 20% by weight, based on the weight of the nanoscale organic UV filters.

8. The composition of claim 1 wherein the composition further contains an auxiliary or additive present in an amount of from 1 to 50% by weight, based on the weight of the composition.

9. The composition of claim 1 wherein the composition is a cosmetic composition.

10. The composition of claim 1 wherein the composition is a pharmaceutical composition.

11. A process for protecting human skin from ultraviolet radiation comprising applying onto the skin a composition containing nanoscale organic UV filters having a mean diameter of from 10 to 300 nm.

12. The process of claim 11 wherein the nanoscale organic UV filters are obtained by:
   (a) providing an organic UV filter starting material;
   (b) dissolving the organic UV starting material in a solvent under supercritical or near-critical condition to form a fluid mixture;
   (c) expanding the fluid mixture through a nozzle into a medium selected from the group consisting of a vacuum, a gas, a liquid, or combinations thereof; and
   (d) evaporating the solvent simultaneously with step (c) to form the nanoscale organic UV filters.

13. The process of claim 11 wherein nanoscale organic UV filters are surrounded by a protective colloid.

14. The process of claim 13 wherein the protective colloid is selected from the group consisting of polyvinyl alcohol, polyethylene glycol, and mixtures thereof.

15. The process of claim 11 wherein the nanoscale organic UV filters are present in the composition in an amount of from 0.1 to 5% by weight, based on the weight of the composition.

16. The process of claim 11 wherein the nanoscale organic UV filters have a mean diameter of from 50 to 150 nm.

17. The process of claim 13 wherein the protective colloid is present in an amount of from 0.1 to 20% by weight, based on the weight of the nanoscale organic UV filters.

18. The process of claim 11 wherein the composition further contains an auxiliary or additive present in an amount of from 1 to 50% by weight, based on the weight of the composition.

19. The process of claim 11 wherein the composition is a cosmetic composition.

20. The process of claim 11 wherein the composition is a pharmaceutical composition.

* * * * *